United States Patent [19]
Cazers et al.

[11] Patent Number: 4,877,782
[45] Date of Patent: Oct. 31, 1989

[54] ZINC CEFTIOFUR COMPLEXES

[75] Inventors: Alexander R. Cazers, Richland; K. Thomas Koshy, Kalamazoo, both of Mich.

[73] Assignee: The Upjohn Company, Kalamazoo, Mich.

[21] Appl. No.: 156,360

[22] Filed: Feb. 16, 1988

[51] Int. Cl.$^4$ .................. C07D 501/56; A61K 31/545
[52] U.S. Cl. ..................................... 514/186; 540/201; 540/222
[58] Field of Search ................ 514/186, 189; 540/222, 540/201

[56]     References Cited
    U.S. PATENT DOCUMENTS
    4,356,264  10/1982  Martin .................................. 514/186

Primary Examiner—Nicholas S. Rizzo
Attorney, Agent, or Firm—John T. Reynolds

[57] ABSTRACT

Zinc ceftiofur complexes, e.g., zinc ceftiofur hydrochloride and zinc ceftiofur sodium complexes, have been found to provide the good antibiotic activity of ceftiofur while providing low dissolution rate and long half-life properties enabling the formulation of improved long term therapy forms of ceftiofur, useful in antibiotic therapy of valuable warm-blooded animals. Pharmaceutical compositions of such zinc ceftiofur complexes and a method of using such zinc ceftiofur complexes in veterinary antibiotic applications are also provided.

5 Claims, No Drawings

ZINC CEFTIOFUR COMPLEXES

INTRODUCTION

This invention relates to zinc derivatives of ceftiofur, a cephalosporin antibiotic, presently of special interest as a veterinary antibiotic in valuable, warm-blooded animals. More particularly, this invention provides new and useful zinc complexes of ceftiofur which improve and expand the usefulness of ceftiofur in field use antibiotic therapy and provides a form of ceftiofur that can be retained longer at the site of injection for longer term therapy of the animal being treated.

BACKGROUND OF THE INVENTION

The cephalosporin antibiotic ceftiofur, which can be named 7-[2-(2-amino-1,3-thiazol-4-yl)-2-methoxyimino)acetamido]-3-[(fur-2-ylcarbonyl)thiomethyl]-3-cephem-4-carboxylic acid, also named 7-[2-(2-amino-1,3-thiazol-4-yl)-2-methoxyimino)acetamido]-3-[2-(furanylcarbonylthiomethyl)-8-oxo-5-thia-1-azabicyclo[4.2.0]oct-2-ene-1-carboxyli acid, and its alkali metal, alkaline earth metal and amine salts of the carboxylic acid group, and easily hydrolyzable esters thereof are described and claimed in Labeeuw et al. U.S. Patent 4,464,367.

Those free acid and alkali metal and amine salt and ester forms of this cephalosporin antibiotic, ceftiofur, are somewhat unstable chemically and are obtained as amorphous compounds which are difficult to purify, and are less desirable to work with in manufacturing pharmaceutical formulations containing them. Those patented salts create salt-solid isolation and salt-solid handling problems in a manufacturing plant which those in the pharmaceutical art would prefer to avoid.

A hydrohalide salt of ceftiofur, particularly the hydrochloride salt thereof, was described and claimed in U.S. patent application Serial No. 664,651 filed 25 October 1984. A corresponding South African Patent No. 85/7613 has been published disclosing such ceftiofur hydrohalide salts.

Those in the art of ceftiofur therapy continue to search for improved forms of ceftiofur including forms of ceftiofur which will not only be acceptable to the health and safety authorities for the contemplated antibiotic therapies but which will permit and provide higher bulk density forms of ceftiofur, easier dispersibility of the selected pharmaceutical form of ceftiofur in aqueous and organic diluents and still not be detrimental to the structure of the parent ceftiofur antibiotic itself.

OBJECTS OF THE INVENTION

It is an object of the invention to provide zinc complexes of ceftiofur and salts thereof as new compounds per se.

It is another object of this invention to provide improved ceftiofur antibiotic zinc complexes which have lower aqueous solubility in water than the sodium and hydrochloride ceftiofur salts but which will provide more easily dispersible in water forms of ceftiofur than the hydrochloride salt of ceftiofur than previously known forms of ceftiofur.

It is another object of this invention to provide pharmaceutical compositions containing a zinc complex of ceftiofur as an active antibiotic ingredient therein.

It is another object of this invention to provide a method or process for treating warm-blooded animal patients in need of ceftiofur antibiotic therapy which comprises administering to such patient an effective amount of one of the zinc ceftiofur complexes of this invention in a pharmaceutical diluent to assist the patient to resist, ward-off or combat infections caused by bacteria susceptible to destruction, neutralization or elimination by ceftiofur from its zinc complex form of this invention.

SUMMARY OF THE INVENTION

Briefly, this invention provides (a) new zinc complexes of ceftiofur and cationic and hydrohalide salts thereof, (b) pharmaceutical formulations thereof, and (c) a method for using these new complexes to take advantage of the chemical and physical properties thereof. The pharmaceutical compositions of this invention comprise the zinc complex of ceftiofur or salt thereof, hereinabove, mixed with one or more pharmaceutically acceptable diluent components. The method of use of this invention comprises administering to a valuable, warm-blooded animal an amount of the zinc complex of ceftiofur effective to assist the animal patient to ward-off, resist, combat or counteract undesired infections by bacteria susceptible to these zinc ceftiofur complex antibiotics.

DETAILED DESCRIPTION OF THE INVENTION

According to this invention, we have discovered that zinc complexes of ceftiofur or a hydrohalide or cationic salt thereof, preferably an alkali metal salt thereof, or a zwitterionic form of ceftiofur, are new useful forms of ceftiofur which extend the useful properties of ceftiofur to applications where lower solubility in standard pharmaceutical fluids and animal body fluids is desirable to lengthen the time particular tissues of the animal body are exposed to the antibiotic effect of the ceftiofur molecule.

Preferably, our invention comprises a complex of an ionic zinc form and a ceftiofur molecule selected from the group consisting of ceftiofur per se, a ceftiofur hydrohalide where the hydrohalide is preferably hydrochloride or hydrobromide, or a ceftiofur cationic salt such as an alkali metal salt, for example, a sodium or potassium salt or an alkaline earth metal salt such as a calcium or magnesium salt or an economical amine salt of ceftiofur such as a triethylamine salt, or the like. We prefer to make our zinc ceftiofur complexes from ceftiofur hydrohalide salts such as the ceftiofur hydrochloride salt or from an alkali metal salt form, e.g., the sodium ceftiofur salt, but they can be made from any of the possible ionic forms of ceftiofur such as the zwitterionic form of ceftiofur, or the like.

The zinc ceftiofur complexes of this invention are not yet known to have a particular structure because it is not yet known whether the zinc of the complexes are bonded, electronically or co-valently to any particular portion of the ceftiofur cephalosporin molecule. [See, however, Page, M.I., "The Mechanisms of Reactions of B-Lactam Antibiotics" in *Acc. Chem. Res.*, 17, pp 144–151 (9184), particularly page 149, and Tomida, H. et al., "Kinetics and Mechanism of Zinc Ion-Mediated Degradation of Cephalosporins in Tromethamine Solution" in *Pharmaceutical Research.*, 4, No. 3, pp. 214-219 (1987) for zinc and metal complexes of other cephalosporins which are said to have more rapid rates of aminolysis and hydrolysis]. In contrast the zinc ceftiofur complexes of this invention have been found to have enhanced stability relative to the above-referenced metallo cephalosporins. We are not sure of the reason why the zinc ceftiofur complexes of this invention are more stable but the presence of sulfur in the 3-position side chain of ceftiofur may favorably influence the stability of the zinc ceftiofur complexes of this invention. However, the evidence from how we made these complexes suggests that there is chemical bonding within the complex between the zinc and the ceftiofur molecules similar to a chelating-type bonding because when the zinc and the ceftiofur or ceftiofur derivative molecules are mixed, there is a precipitation from those mixtures of zinc and ceftiofur containing entities which we have found are antibiotically active and which have new desirable low solubility properties which suggest a new longer acting form of ceftiofur is obtainable with these complexes. For example, we have found that the zinc ceftiofur complex made from ceftiofur hydrochloride in non-micronized form is less soluble than the ceftiofur hydrochloride. The solubility of such zinc ceftiofur hydrochloride complex is about 85% of that of non-micronized ceftiofur hydrochloride bulk drug and is 73% of the solubility of the micronized ceftiofur hydrochloride. More interestingly, the rate of dissolution of the zinc ceftiofur hydrochloride complex is much slower compared to ceftiofur hydrochloride. For example, in 20 minutes under comparable equilibration conditions 74% of unmicronized ceftiofur hydrochloride is in aqueous solution compared to only 48% of the zinc ceftiofur hydrochloride complex. Similarly, the solubility of unmicronized zinc ceftiofur sodium complex in water after 20 minutes 9s 47% compared to 100% for ceftiofur sodium, under comparable equilibration conditions. For the above reasons we do not wish to be bound by any particular or possible chemical bonding structures in these complexes. We have not yet obtained a crystalline form of these zinc ceftiofur complexes which can be analyzed exactly to pinpoint the possible chemical structures of these complexes. However, we do know that these complexes are of uniform elemental composition.

The invention here includes our finding that these zinc ceftiofur complexes are uniquely adapted for incorporation into pharmaceutical compositions. This finding appears to directly contradict prior scientific publications (e.g., the Page et al publication, regarding metal complexes of other cephalosphorins) that such metallocephalosporin complexes are inordinately labile, i.e., they decompose and lose their antibacterial properties, and thus are of singular interest only for chemical mechanistic studies of zinc dependent B-lactamase cephalosporin degradation processes. Such references divert attention away from our discovery of the advantages to be had using zinc ceftiofur complexes in pharmaceutical formulations for treating valuable warm-blooded animal patients. We believe that the low solubility of zinc ceftiofur complexes of this invention in water illustrates the great potential for the development of improved sustained release forms of the ceftiofur antibiotic for animal use. Although we do not yet have quantitative data on the solubility of the zinc ceftiofur complexes of this invention in various organic solvents, we known that these zinc ceftiofur complexes are practically insoluble in most common organic solvents [except dimethylformamide (DMF)]and pharmaceutically useful vegetable oils. These low solubility properties should make these zinc ceftiofur complexes an attractive form of ceftiofur for depot type administration formulations where it is desired to maintain dosages of the ceftiofur antibiotic close to the site of infection in the animals being treated.

Further, the zinc ceftiofur complexes of this invention have advantageous, heavier bulk density properties relative to the non-zinc complexed forms of the same ceftiofur entities. For example, the bulk density of the zinc ceftiofur sodium complex from water is about 0.19 g./ml. compared to 0.11 g./ml. for ceftiofur sodium salt. The bulk density of zinc ceftiofur hydrochloride of this invention is about 0.24 g./ml. compared to 0.15 for the non-complexed ceftiofur hydrochloride salt. This higher bulk density property is advantageous in pharmaceutical formulation preparation. The zinc ceftiofur sodium complex and the zinc ceftiofur hydrochloride complex materials are obtainable as granular powders. These granular powders are readily dispersible in water (whereas the precursor ceftiofur hydrochloride salt is less well adapted for distribution in pharmaceutical aqueous vehicle formulations) and in common pharmaceutical organic solvents and in vegetable oils.

The zinc ceftiofur complexes of this invention can be made by reacting the selected form of ceftiofur, preferably ceftiofur per se, an alkali metal salt of ceftiofur, e.g., the sodium or potassium ceftiofur salt, or a hydrohalide salt of ceftiofur, e.g., the diluent such as an alkanol having from one to six carbon atoms or similar diluent with a similar solution of a zinc salt of an organic acid, such as a zinc alkanoate salt having from one to six carbon atoms in the alkanoate moiety, e.g., zinc formate, zinc acetate, zinc propionate, zinc butanoate, zinc hexanoate in their various isomeric forms, zinc benzoate, or a zinc methanesulfonate, and the like, preferably in slightly excess stoichiometric proportion of the zinc salt to ensure as complete a reaction as possible of the more expensive ceftiofur reactant to form the respective zinc ceftiofur complex which usually precipitates from the reaction mixture. The resulting precipitated zinc ceftiofur complex is then recovered from the reaction mixture by conventional methods such as filtration or centrifugation procedures and then purified to at least some degree by washing with one or more wash liquids or solvents for byproducts, dried to a constant weight and then such complex is ready for formulation into any of various possible pharmaceutical delivery vehicle compositions, which are exemplified by the detailed examples hereinbelow.

The term "dosage unit form" are used in this specification and in the claims refers to physically discrete units suitable as unitary dosages for mammalian subjects, each unit containing as the essential active ingredient a predetermined quantity of a compound of this invention with the required pharmaceutical means which adapt said ingredient for systemic or topical administration. The specification for the novel dosage unit forms of this invention are dictated by and directly dependent on the physical characteristics of the essential active ingredient and the particular effect to be achieved in view of the limitations inherent in the art of compounding such an essential active material for beneficial effects in humans and animals as disclosed in detail in this specification. Examples of suitable dosage unit forms in accordance with this invention are tablets, capsules, orally administered liquid preparations in suitable liquid vehicles, sterile preparations in suitable liquid vehicles for intramuscular and intravenous administration, suppositories and sterile dry preparations for the extemporaneous preparation (mixing just prior to administration) of sterile injectable preparations in a suitable liquid vehicle and topical ointments and creams. Suitable solid diluents or carriers for the solid oral pharmaceutical dosage unit forms are selected from the group consisting of lipids, carbohydrates, proteins and mineral solids, for example, starch, sucrose, lactose, kaolin, dicalcium phosphate, gelatin, acacia, corn syrup, corn starch, talc and the like. Capsules, both hard and soft, are filled with compositions of this antibiotic active ingredient in combination with suitable diluents and excipients, for example, edible oils, talc, calcium carbonate and the like and also calcium stearate. Liquid preparations for oral administration are prepared in water or aqueous vehicles which advantageously contain suspending agents, for example, methylcellulose, alginates, tragacanth, pectin, kelgin, carragenan, acacia, polyvinylpyrrolidone, polyvinyl alcohol, and the like, to increase the viscosity of the composition. In the case of injectable forms, the injectable formulation must be sterile and must be fluid to the extent that easy syringeability exists. Such preparations must be stable under the conditions of manufacture and storage, and ordinarily contain in addition to the principal solvent or suspending liquid, preservatives in the nature of bacteriostatic and fungistatic agents, for example, parabens, chlorobutanol, benzyl alcohol, benzoic acid, phenol, thimerosal, and the like to preserve the composition against microorganisms. In many cases, it is preferable to include osmotically active agents, for example, sugars or sodium chloride in isotonic concentrations in water pharmaceutical diluent systems. Carriers and vehicles include vegetable oils, dimethylacetamide, dimethylformamaide, ethyl lactate, ethyl carbonate, isopropyl myristate, ethanol, polyols, for example, glycerol, propylene glycol, liquid polyethylene glycol, and the like. Any solid preparations for subsequent extemporaneous preparation of sterile injectable preparations are sterilized, by exposure of steam, cobalt 60 irradiation, or by exposure to a sterilizing gas, for example, ethylene oxide. The aforesaid carriers, vehicles, diluents, surfactants, excipients, preservatives, isotonic agents and the like constitute the pharmaceutical means which adapt the preparations for systemic administration.

In these pharmaceutical compositions it may be desirable to include a viscosity-increasing agent such as sodium carboxymethylcellulose (sodium CMC). Other suitable viscosity-increasing agents can be substituted for sodium CMC.

The pharmaceutical dosage unit forms of the compounds of this invention are prepared in accordance with the preceding general description to provide from about 1 mg. to about 500 mg. of the essential active ingredient per dosage unit form, which as aforesaid may be in the form of a semi-solid or solid, topical, oral or rectal preparation, a liquid oral preparation, an injectable preparation including liquid preparations and solid dry preparations for extemporaneous reconstitution to a liquid injectable preparation. The amount of the essential active ingredient provided in the pharmaceutical dosage unit forms is that amount sufficient to obtain antibiotic effects within the aforesaid effective nontoxic range. Expressed otherwise, when used systemically, an amount of the essential active ingredient is provided to a recipient within a range from about 0.2 mg./kg. to about 100 mg./kg. of body weight of the recipient.

Preferred dosages for most applications are 0.2 mg./kg. to 10.0 mg./kg. of body weight depending upon the animal being treated. In a topical, semi-solid ointment formulation the concentration of the active ingredient may be 1%–20%, preferably 5%–10% in a carrier, such as a pharmaceutical cream base.

The useful pharmaceutical dosage unit forms of these compounds in pharmaceutical formulations are preferably adapted for systemic administration to obtain antibiotic effects comprising an effective, non-toxic amount of the Formula 1 salt.

Further, the invention relates to methods of obtaining antibiotic effects in mammals, for example, valuable warm-blooded animals such as dogs, cats, horses, and other commercially valuable animals, by administering systemically to the mammals the aforesaid pharmaceutical dosage units forms supplying an effective, non-toxic amount for antibiotic effects.

The invention is further exemplified and described by the following detailed examples, which are not intended to be limiting.

EXAMPLE 1

Zinc Ceftiofur Complex From Sodium Ceftiofur (Compound I) From Water

A 0.22 g (0.4 mmole) portion of sodium ceftiofur was dissolved in 8 ml. of water with the aid of a few drops of 0.1 M sodium bicarbonate solution. The mixture was cooled in an ice bath. To this cooled solution there was added dropwise with stirring five ml. of a solution containing 0.44 g (2 mmole) of zinc acetate, previously cooled in an ice bath. A white precipitate resulted. The reaction mixture was allowed to stand for 1.5 hours in an acetone/ice bath and then the mixture was centrifuged at about 2000 RPM and the supernatant liquid was discarded. The separated precipitate was washed with cold water three times, discarding the supernatant wash water each time. The resulting zinc ceftiofur sodium complex was suspended in water and lyophilized to obtain as product 120 mg. of the zinc ceftiofur sodium complex as an off-white powder having a purity of about 76% by an HPLC analytical method.

EXAMPLE 2

Zinc Ceftiofur Sodium Complex From Methanol (Compound I)

A 11 g. (20 mmole) portion of sodium ceftiofur was dissolved in a mixture of 50 ml. of water and 150 ml. of methanol. Separately, a 20 g. portion of zinc diacetate dihydrate was dissolved in a mixture of 20 ml. of water and 100 ml. of methanol. The zinc diacetate dihydrate solution was added with stirring to the sodium ceftiofur solution contained in a 500 ml. beaker. The resulting reaction mixture was allowed to stand for about 45 minutes in an ice bath (0° C.) and then filtered through a coarse sintered glass funnel to separate the precipitate which had formed. The separated precipitate was washed with about 120 ml. of cold methanol and then dried in a vacuum at room temperature for 64 hours. There was thus obtained 6 g. of the zinc ceftiofur sodium complex as a granular powder, having a purity of 94.8% (HPLC method), from methanol.

EXAMPLE 3

Zinc Ceftiofur Hydrochloride Complex (Compound II)

A 11 g. (20 mmole) portion of ceftiofur hydrochloride salt was dissolved in 150 ml. of methanol. Separately, a 20 g. portion of zinc diacetate dihydrate was dissolved in 20 ml. of water plus 150 ml. of methanol. While stirring, the zinc diacetate dihydrate solution was added to the ceftiofur hydrochloride solution in a 500 ml. beaker. The reaction mixture was allowed to stand at 0° C. for 45 minutes and then filtered through a coarse sintered glass funnel. The separated precipitate was washed with 120 ml. of cold methanol and then dried in a vacuum for 64 hours. The resulting zinc ceftiofur hydrochloride complex weighed 9 g. and was a granular powder, having a purity of about 94% (HPLC method).

The formulation of the zinc ceftiofur complexes of this invention into pharmaceutical compositions can be done by conventional methods. The following examples illustrate various useful formulations for these new complexes.

EXAMPLE 4

Sterile Parenteral Suspension

| Sterile Vehicle | |
|---|---|
| Part I | |
| Polysorbate 80, N.F. | 0.1 to 10 gms. |
| Sodium Carboxymethylcellulose low viscosity | 2 to 20 gms. |
| Benzyl Alcohol | 9.1 gms. |
| Benzoic Acid | 0.2 to 2.0 gms. |
| Povidone | 1 to 10 gms. |
| Sodium Chloride, Fine Crystals Reagent, if needed, | up to 9 gms. |
| Hydrochloric Acid, Reagent Grade adjust pH to approx. | 6.0 |
| Water for Injection | q.s. to 1000 cc. |
| Part II | |
| Compounds I and II from Example 1, 2 or 3, powder | 1.0 to 100 gms. |
| Vehicle Part I | q s. adjust 1000 cc. |

Directions:

Part I

All of the ingredients are dissolved in water and the vehicle sterilized by filtration. Part II Aseptically add sterile Compound I or II from Example 1, 2 or 3 in sufficient vehicle to make 900 mls. Stir the suspension and pass through colloid mill to a uniform consistency. Add sufficient vehicle to make 1000 mls.

EXAMPLE 5

Sterile Parenteral Suspension

| Sterile Vehicle | |
|---|---|
| Part I | |
| PEG 3350 NF | 5 to 120 gms. |
| Benzyl Alcohol | 9.1 gms. |
| Benzoic Acid | 0.2 to 2.0 gms. |
| Polysorbate 80 NF Food Grade | 1 to 5 gms. |
| Sodium Chloride Fine Crystals Reagent | 0.5 to 10 gms. |
| Hydrochloric Acid, Reagent Grade | q.s. adjust pH to approx. 6.0 |
| Water for Injection | q s. to 1000 cc. |
| Part II | |
| Compounds I or II from Example 1, 2 or 3 powder | 1 to 100 gms. |
| Vehicle Part I | q.s. adjust 1000 cc. |

Directions:

Part I

All of the ingredients are dissolved in water and pH adjusted to approximately 3.0, and the vehicle sterilized by filtration.

Part II

Aseptically add sterile Compound I or Compound II from Example 1, 2 or 3 in sufficient vehicle from Part I to make 900 mls. Stir the suspension and pass through a colloid mill to a uniform consistency. Add sufficient vehicle to make 1000 mls.

EXAMPLE 6

Sterile Extemporaneous Parenteral Suspension (Aqueous)

| Sterile Vehicle | |
|---|---|
| Part I | |
| Benzyl Alcohol | 9.1 gms. |
| or | |
| Benzoic Acid | 0.2 to 2.0 gms. |
| Carboxymethylcellulose Sodium USP low viscosity or any other viscosity inducing agent | 1.0 to 20.0 gms. |
| Sodium Chloride Fine Crystals, Reagent Grade | 0.5 to 10 gms. |
| Hydrochloric Acid, Reagent Grade | q.s. adjust pH to approx. 6.0 |
| Water for Injection | |
| Part II Amount per Vial | |
| Sterile Compound I or II from Example 1, 2 or 3 in a 10 to 100 ml. glass vial | 0.01 to 1.5 gm. |

Directions:

Part I

All of the ingredients are dissolved in water, and pH adjusted to approximately 5.6 to 6.1, preferably about 6.0. Vehicle sterilized by filtration and packaged in appropriate glass vials.

Part II

Sterile powdered Compound I or II is packaged aseptically in sterile vials and the final container(s) are sterilized by Cobalt 60 irradiation.

EXAMPLE 7

Sterile Extemporaneous Parenteral Suspension

| Sterile Vehicle | |
|---|---|
| Part I | |
| Methylparaben | 1.0 to 2.7 gms. |
| Propylparaben | 0.1 to 0.5 gm. |
| Povidone | 1 to 10 gms. |
| Sodium Chloride Fine Crystals Reagent Grade | 0.5 to 10 gms. |
| 20% Solution Hydrochloric acid | q.s. adjust pH to approx. 3.0 |
| Water for Injection | q.s. to 1000 cc. |
| Part II Amount Per Vial | |
| Sterile Compound I or II from Example 1, 2 or 3 in a 10 to 100 ml. glass vial | 0.01 to 1.5 gm. |

Directions

Part I

Methylparaben and propylparaben are dissolved in boiling water. Then all of the ingredients dissolved in water, and pH adjusted to approximately 5.6 to 6.2, preferably about 6.0. Vehicle sterilized by filtration and packaged in appropriate glass vials.

Part II

Sterile Compound I or II is packaged aseptically in sterile vials and sterilized by Cobalt 60 irradiation.

EXAMPLE 8

Extemporaneous Parenteral Suspension (Aqueous)

| Sterile Vehicle | |
| --- | --- |
| Part I | |
| Polyethylene Glycol 3350 NF | 5 to 120 gms. |
| Polyvinyl Pyrrolidone | 1 to 10 gms. |
| Quatresin ® myristyl gamma picolinium chloride | 0.1 to 2.0 gms. |
| Sodium Chloride, Fine Crystals Reagent Grade | 0.5 to 10 gms. |
| 20% Solution Hydrochloric Acid | q.s. adjust pH to approx. 6.0 |
| Water for Injection | q.s. to 1000 cc. |
| Part II Amount Per Vial | |
| Sterile powdered Compound I or II from Example 1, 2 or 3 (milled or micronized) in a 10 to 100 ml. glass vial | 0.01 to 1.5 gms. |

Directions

Part I

All of the vehicle ingredients are dissolved in water and pH adjusted to approximately 5.6 to 6.1, preferably about 6.0. Vehicle sterilized by filtration and packaged in appropriate glass vials.

Part II

Sterile powdered Compound I or II is packaged aseptically in sterile vials and sterilized by Cobalt 60 irradiation.

Thereafter, just prior to use, the vehicle and drug components are mixed and then administered to the animal.

EXAMPLE 9

Sterile Non-aqueous Parenteral Suspension

| | |
| --- | --- |
| Powdered Compound I or II from Example 1, 2 or 3 (milled or micronized) | 1 to 100 gms. |
| Chlorobutanol Anhydrous - preservative or | 5.25 gms. |
| Benzyl Alcohol | 9.25 gms. |
| Corn Oil Glyceryl Monostearate Gel or | |
| Cottonseed Oil Glyceryl Monostearate Gel | q.s. to 1000 cc. |

Directions

Preservative is dissolved in sufficient oily gel to make 800 cc. Compound I or II is added and the suspension is colloid milled to a uniform consistency. Add sufficient gel to make 1000 mls. After packaging into glass vials, the suspension is sterilized by Cobalt irradiation or by any other suitable method.

EXAMPLE 10

Sterile Non-Aqueous Parenteral Suspension

| | |
| --- | --- |
| Compound I or II from Example 1,2 or 3 (milled or micronized) | 1 to 100 gms. |
| Chlorobutanol Anhydrous or | 5.25 gms. |
| Benzyl Alcohol | 9.25 gms. |
| Corn Oil USP or | q.s. adjust 1000 cc. |
| Cottonseed oil | q.s. adjust 1000 cc. |

Directions

Preservative is dissolved in sufficient oil to make 800 cc. Compound I or II is added and the suspension is colloid milled to a uniform consistency to break the aggregates. Add sufficient amount of oil to make 1000 mls. Stir and package into glass vials. The suspension can be sterilized by Cobalt 60 irradiation or sterile powdered Compound I or II can be added to sterile vehicle and manufactured following aseptic procedure(s).

EXAMPLE 11

Sterile Extemporaneous Parenteral Suspension (Non-aqueous Gel) - Controlled Release Formulation

| Sterile Vehicle | |
| --- | --- |
| Part I 1000 | |
| Benzyl Alcohol - preservative or | 9.0 to 9.25 gms. |
| Chlorobutanol | 5.0 to 5.25 gms. |
| Corn Oil Glyceryl Monostearate Gel or | 1000 cc. |
| Cottonseed Oil Glyceryl Monostearate Gel | 1000 cc. |
| Part II 100 Vials | |
| Powdered Compound I or II from Example 1, 2 or 3 (milled or micronized) | 1 to 100 gms. |

Directions

Part I

Preservative is dissolved in sufficient gel and the gel is filled into vials asceptically and the vials sealed. These vials will be packaged with the vials of Part II as companion package.

Part II

0.01 to 1.0 gm. of powdered Compound I or II or sterilized powdered Compound I or II is packaged in a sterile glass vial and the vials sealed. If the powdered Compound I or II is non-sterile, then the packaged vials will be sterilized by Cobalt 60 irradiation.

Prior to dosing appropriate amounts of Part I diluent will be added to Part II sterile powder and shaken until homogeneous.

EXAMPLE 12

Sterile Extemporaneous Parenteral Suspension (Non-aqueous)

| Sterile Vehicle | |
| --- | --- |
| Part I 1000 | |
| Benzyl Alcohol - preservative or | 9.0 to 9.25 gms. |
| Chlorobutanol | 5.0 to 5.25 gms. |
| Corn Oil, USP or | q.s. adjust 1000 cc. |
| Cottonseed Oil, USP | q.s. adjust 1000 cc. |
| Part II 100 Vials | |
| Compound I or II from Example 1, 2 or 3 (milled and micronized) | 50 to 100 gms. |

Part I

Preservative is dissolved in the oil, and the solution sterilized by filtration. The sterile solution is filled into vials and the vials sealed. These vials will be packaged with the vials of Part II as companion package.

Part II 0.5 to 1.0 gm. of Compound I or II or sterilized Compound I or II is packaged in a sterile glass vial and the vials sealed. If the Compound I or II is non-sterile, then the packaged vials will be sterilized by Cobalt 60 irradiation.

Prior to dosing appropriate amount of Part I diluent will be added to Part II sterile Compound I or II and shaken until uniformly mixed.

EXAMPLE 16

Suppositories

Formulation for a 2 gm. suppository containing 62.5 mg. of powdered Compound I or II is given. However, any size suppository can be manufactured using any amount of Compound I or II and appropriate amounts of excipients at the same ratio as indicated below.

| Lot Size 12 | |
|---|---|
| Compound I or II from Examples 1, 2 or 3 (milled or micronized) | 7.5 gm. |
| PEG-400 | 144 ml. |
| PEG-8000 | 96 gm. |

Directions

Measure out 144 ml. of PEG-400 and place in a container suitable for heating. Add 96 gms. of PEG-8000 (melting point 140° F.) to the PEG-400 solution and melt over a hot water bath approximately two minutes or until there is a clear solution.

Add the 7.5 g of the Compound I or II and stir until dispersed. Pour the mix into the mold and let set. Chill the mold. Remove suppositories after they set up 15–30 minutes at room temperature. Sterile suppositories can be manufactured with sterile raw materials and observing aseptic conditions during manufacturing, or can be sterilized by Cobalt 60 irradiation.

EXAMPLE 14

Suppositories

Suppositories can also be manufactured from excipients such as cocoa butter, Suppocire TM AM, Suppocire TM AS$_2$, and Suppocire TM AT, Suppocire BT or Suppocire CT brand of C$_8$ to C$_{10}$—saturated fatty acid glycerides.

Formula for a 2 gm. suppository containing 62.5 mg. of Compound I or II is given; however, any size suppository can be manufactured using any desired amount of powdered Compound I or II and appropriate amount of excipient.

| Lot Size 12 | |
|---|---|
| Compound I or II from Example 1, 2 or 3 (milled or micronized) Sterile | 0.750 gm. |
| Suppocire AM or AS$_2$, or AT, or BT or CT | 23.25 gm. |

Directions

Weight the Suppocire TM diluent in a container suitable for heating. Melt (45° C. temperature) over a hot water bath for approximately two minutes or until there is a clear solution (microwave oven can also be used instead of the water bath). Sterilize by filtration. Add sterile Compound I or II and stir until dispersed. Pour the mix into the cold mold. After two to four minutes, the surplus of the casting is eliminated by scraping. The temperature and time of cooling must be governed according to the type of formula. The circulating cold air should come in contact with all faces of the mold. Release from the mold must be gentle. Sterile suppositories can be manufactured with sterile raw materials and observing aseptic conditions during manufacturing, or can be sterilized by Cobalt 60 irradiation.

EXAMPLE 15

Capsules

One thousand two-piece hard gelatin capsules for oral use, each containing 50 mgs. of activity of the Compound I or II, are prepared from the following types and amounts of materials:

| 1000 | |
|---|---|
| Compound I or II from Example 1, 2 or 3 (50 gms. equivalent of ceftiofur) or Coated with Carnauba Wax ® or White Wax | 75 gm. |
| Talc and/or Magnesium Stearate | 2.5 gms. |

Wax coated powdered Compound I or II will have controlled release properties. The materials are thoroughly mixed and then encapsulated in the usual manner. Different strength capsules can be prepared by changing the amounts of powdered Compound I or II.

EXAMPLE 16

Antibiotic Activity of the Zinc Ceftiofur Complexes of This Invention

A zinc ceftiofur hydrochloride complex of this invention was tested and compared for antibiotic potency against ceftiofur hydrochloride per se and against sodium ceftiofur in standard mouse challenge tests against the representative bacterial organisms Salmonella typhimurium UC6164 and Pasteurella multocida UC9581 to determine their ED$_{50}$ numbers.

Each test compound was suspended or dissolved in sterile Vehicle 122 (0.025% carboxymethylcellulose in water) to a starting test concentration sufficient to provide in the first set of test animals a concentration of the test drug of 2 mg./kg. Portions of each such test drug formulation were diluted seriatim 50:50 v/v with water to reduce the concentration of the test drug in the test animal to 1 mg./kg., then to 0.5 mg./kg., to 0.25 mg./kg. and finally to 0.125 mg./kg. Sets of mice were injected with the test dilutions of the test drugs subcutaneously once or three times after injecting challenge doses lethal doses of one of the above-named bacterial organisms. The sets of animals were observed over six days to determine the number of surviving mice. The mortality ratios were noted and the ED$_{50}$ values were calculated for each test drug by standard methods. The test results are summarized in the table which follows.

TABLE I

| Organism | No. of LD50's | No. of Treatments | ED50 (mg./kg./day) | | |
|---|---|---|---|---|---|
| | | | C—HCl | Zn—C—HCl | C—Na |
| UC6164 | 1000 | 3X | 2.3 (1.5–4.0) | 2.1 (1.4–3.1) | ND |
| | 579 | 1X | 1.7 (1.0–2.8) | 1.0 (0.6–1.7) | ND |

TABLE I-continued

| Organism | No. of LD50's | No. of Treatments | C—HCl | ED50 (mg./kg./day) Zn—C—HCl | C—Na |
|---|---|---|---|---|---|
|  | 1000 | 1X | 1.3 (0.7–2.1) | 3.3 (0.7–2.1) | 1.1 (0.6–1.9) |
| UC9581 | 27 | 3X | 0.3 (0.2–0.4) | 0.4 (0.2–0.5) | ND |
|  | 303 | 1X | 0.3 (0.2–0.4) | 0.3 (0.2–0.4) | 0.3 (0.2–0.4) |

Footnotes:
ED50 values are within 95% confidence limits.
All values are adjusted for drug potency as provided.
C—HCl means ceftiofur hydrochloride.
Zn—C—HCl means zinc ceftiofur hydrochloride complex of this invention.
C—Na means ceftiofur sodium salt.
ND means not determined.

These above $ED_{50}$ number values indicate a potent antibiotic protection by the zinc ceftiofur hydrochloride complex of this invention, similar to that of the ceftiofur hydrochloride and the sodium ceftiofur salts.

In addition, dissolution rate curves for percent of the ceftiofur complexes of this invention dissolved over time compared to the dissolution rates of sodium ceftiofur and ceftiofur hydrochloride over the same time periods indicate that the zinc ceftiofur complexes of this invention generally take longer to dissolve, particularly over the first part of the dissolution test time, than do the ceftiofur hydrochloride and sodium ceftiofur salts. The sodium ceftiofur salt itself dissolves quite quickly in water. These dissolution rate test comparisons suggest that the zinc ceftiofur complexes of this invention would be a better slow release form of ceftiofur and that it has a longer half-life than do the ceftiofur hydrochloride and the ceftiofur sodium salts. Knowing this enables formulators of ceftiofur to pick a preferred ceftiofur salt or complex entity and an appropriate pharmaceutical formulation that will allow the drug to be retained at the site of injection or application longer for extended drug treatment.

We claim:

1. A complex of ionic zinc and a ceftiofur molecule selected from the group consisting of ceftiofur per se, a ceftiofur hydrohalide where the halide is chloride or bromide and a ceftiofur alkali metal or alkaline earth metal salt where the metal salt ion is selected from the group consisting of sodium, potassium, calcium and magnesium.

2. A complex according to claim 1 which is a complex of bivalent zinc and a ceftiofur hydrochloride.

3. A complex according to claim 1 which is a complex of bivalent zinc and an alkali metal salt of ceftiofur.

4. A pharmaceutical composition comprising (a) a zinc ceftiofur complex according to claim 1 as an essential antibiotic ingredient therein and (b) one or more pharmaceutically acceptable diluent carrier ingredients.

5. A method for treating a warm-blooded animal patient to resist, ward-off, or combat undesired biological pathogen infections in said animal which comprises
    administering to said animal patient an effective amount of a pharmaceutical composition containing a zinc ceftiofur complex as defined in claim 1.

* * * * *